United States Patent
O'Toole et al.

(10) Patent No.: US 12,283,144 B2
(45) Date of Patent: Apr. 22, 2025

(54) SYSTEM TO EVALUATE AND MANAGE PEOPLE ENTERING A BUILDING BASED ON INFECTION RISK DATA, ENVIRONMENTAL DATA, AND BUILDING ENTRANT HEALTH DATA

(71) Applicant: Tyco Fire & Security GmbH, Neuhausen am Rheinfall (CH)

(72) Inventors: Eamonn Jerry O'Toole, Ballincollig (IE); Ronan Fineen Hennessy, Carrigaline (IE); Róisín Ann O'Brien, Glanmire (IE)

(73) Assignee: TYCO FIRE & SECURITY GMBH, Neuhausen am Rheinfall (CH)

( * ) Notice: Subject to any disclaimer, the term of this patent is extended or adjusted under 35 U.S.C. 154(b) by 295 days.

(21) Appl. No.: 17/532,815

(22) Filed: Nov. 22, 2021

(65) Prior Publication Data

US 2023/0162546 A1 May 25, 2023

(51) Int. Cl.
*G16H 40/20* (2018.01)
*G06N 7/01* (2023.01)
(Continued)

(52) U.S. Cl.
CPC .......... *G07C 9/00563* (2013.01); *G06N 7/01* (2023.01); *G08B 7/066* (2013.01); *G16H 40/20* (2018.01); *G16H 50/80* (2018.01)

(58) Field of Classification Search
CPC .......... G06N 20/00; G06N 7/01; G06N 20/10; G06N 3/006; G06N 3/084; G06N 3/126; G06N 5/01; G06N 5/04; G06N 5/041; G07C 9/00563; G07C 9/10; G07C 9/20; G07C 9/27; G07C 9/257; G07C 9/00; G07C 9/37; G07C 13/00; G07C 9/15; G07C 9/25; G07C 9/253; G07C 9/32; G07C 9/38; G08B 7/066; G08B 21/245; G08B 21/0476; G08B 21/22; G08B 3/10; G16H 40/20; G16H 50/20; G16H 50/30; G16H 50/80; G16H 10/20; G16H 10/60; G16H 40/63;
(Continued)

(56) References Cited

U.S. PATENT DOCUMENTS

| 10,074,226 | B2 * | 9/2018 | Meganathan | B64U 10/14 |
|---|---|---|---|---|
| 2014/0006451 | A1 * | 1/2014 | Mullis | G06Q 20/18 707/784 |

(Continued)

*Primary Examiner* — Dionne Pendleton
(74) *Attorney, Agent, or Firm* — Foley & Lardner LLP

(57) ABSTRACT

A method for providing access into a building is shown. The method includes receiving an indication that a potential building occupant is requesting access into the building. The method includes providing input data into a probabilistic model, the input data comprising current health data of the potential building occupant obtained in response to receiving the indication. The method includes analyzing, via the probabilistic model, relationships between a plurality of weighted variables within the probabilistic model to determine an entry decision for the potential building occupant, wherein each of the plurality of weighted variables are representative of subsets of the input data. The method includes, in response to the entry decision permitting the building occupant to enter the building, providing a control signal to a security system to permit access to the building for the building occupant.

18 Claims, 10 Drawing Sheets

(51) Int. Cl.
  *G07C 9/00* (2020.01)
  *G08B 7/06* (2006.01)
  *G16H 50/80* (2018.01)

(58) Field of Classification Search
  CPC ........ G16H 50/70; G16H 10/40; G16H 15/00;
      G16H 10/65; G16H 40/67; G16H 80/00;
      G16H 20/13; G16H 30/40; G16H 50/50;
      H04L 67/125; H04L 63/08; H04L
      63/0861; H04L 2209/80; H04L 63/067;
      H04L 63/0838; H04L 63/101; H04L
      9/0816; H04L 9/321; H04B 1/3822;
      G06Q 20/18; G06Q 20/3278; G06Q
      20/40145; G06Q 30/02; G06Q 50/00;
      G06Q 50/22; G06Q 10/06; G06Q 50/265;
      G06Q 30/0185; G06Q 50/01; G06Q
      10/02; G06Q 10/10; G06Q 10/103; G06Q
      10/105; G06Q 10/107; G06Q 20/047;
      G06Q 20/4014; G06Q 2230/00; G06Q
      2240/00; G06Q 30/018; G06Q 50/205;
      G06Q 50/26; A61L 2/0088; A61L 2/26;
      A61L 2202/15; H04W 4/33; H04W 4/38;
      H04W 4/029; H04W 4/90; H04W 12/069;
      H04W 12/77; H04W 12/63; H04W 12/64;
      H04W 4/021; G06K 19/06037; G06K
      7/1417; G06K 19/06112; G06K 19/0614;
      G06K 19/06168; G06K 7/10297; G06K
      7/1095; G06K 7/1413; G06F 21/6245;
      G06F 21/31; G06F 21/33; G06F 21/32;
      G06F 21/36; G06F 21/45; G06F 21/602;
      G06F 21/62; A61B 5/0022; A61B
      2503/12; A61B 2562/08; A61B 5/01;
      A61B 5/015; A61B 5/055; A61B 5/0816;
      A61B 5/0823; A61B 5/1172; A61B
      5/4011; A61B 5/4017; A61B 5/4833;
      A61B 5/6887; A61B 5/7405; A61B
      5/746; A61B 5/7465; A61B 6/032; A61B
      8/08; A61B 8/48; A61B 8/5207; G06V
      30/10; G06V 30/414; G06V 40/171;
      G06V 10/143; G06V 20/52; G06V 20/53;
      G06V 40/166; Y02A 90/10; A41D 13/11;
      A41D 13/1192; A62B 18/025; A62B
      7/10; C12Q 1/04; H04N 23/23; H04N
      5/33; G07F 17/0092; G06T 2207/30201;
      G06T 7/136; G01N 2021/6421; G01N
      21/6428; G01J 5/0025; E06B 3/903; E05Y
      2201/434; E05Y 2400/30; E05Y
      2400/822; E05Y 2800/266; E05Y
      2900/116; E05Y 2900/132; E05G 5/003;
      E05G 5/02; E05F 15/00; E05F 15/42;
      E05F 15/632
  See application file for complete search history.

(56) References Cited

U.S. PATENT DOCUMENTS

| | | | | |
|---|---|---|---|---|
| 2020/0126664 A1* | 4/2020 | Sato | ............. | G16H 50/20 |
| 2021/0233658 A1* | 7/2021 | Van Assel | ............. | G16H 70/60 |
| 2021/0335072 A1* | 10/2021 | Caldwell | ............. | G07C 9/00563 |
| 2022/0254481 A1* | 8/2022 | Avisar | ............. | G16H 40/20 |
| 2023/0154263 A1* | 5/2023 | Toiv | ............. | G07C 9/28 |
| | | | | 340/5.61 |

* cited by examiner

SYSTEM TO EVALUATE AND MANAGE PEOPLE ENTERING A BUILDING BASED ON INFECTION RISK DATA, ENVIRONMENTAL DATA, AND BUILDING ENTRANT HEALTH DATA

BACKGROUND

The present disclosure relates to building management systems. More specifically, the present disclosure relates to building management systems that employ an access control system to make entry decisions for potential building occupants.

In most building systems, potential building occupants are only evaluated to determine if they are a valid member of the building's access directory at a certain time. Existing building systems generally are not configured to use access control systems to determine if increased health risks are posed by a person attempting to enter a building.

SUMMARY

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

One implementation of the present disclosure is a method for providing access into a building. The method includes receiving an indication that a potential building occupant is requesting access into the building. The method further includes providing input data into a probabilistic model, the input data including current health data of the potential building occupant obtained in response to receiving the indication. The method further includes analyzing, via the probabilistic model, relationships between a plurality of variables within the probabilistic model to determine an entry decision for the potential building occupant, each of the plurality of variables are representative of subsets of the input data. The method further includes, in response to the entry decision permitting the potential building occupant to enter the building, providing a control signal to a security system to permit access to the building for the potential building occupant.

In some embodiments, analyzing the relationships between the plurality of variables within the probabilistic model includes determining the subsets of the input data and dependencies between the subsets of the input data, wherein the plurality of variables represent the subsets of the input data and the relationships between the plurality of weighted represent the dependencies between the subsets of the input data, determining a joint probability distribution between two or more of the plurality of variables, using the joint probability distribution to determine a probability of the potential building occupant having an infectious disease, and determining the entry decision for the potential building occupant.

In some embodiments, the input data further includes infectious risk data and profile data from a profile associated with the potential building occupant. In some embodiments, the subsets of the input data include at least one of local infection rate, contact tracing status, vaccination status, and temperature.

In some embodiments, the probabilistic model is a Bayesian network model. In some embodiments, the plurality of variables are each weighted based on a likelihood that each of the plurality of variables would affect a probability of the potential building occupant having an infectious disease.

In some embodiments, the method further includes, in response to the entry decision permitting the potential building occupant to enter the building, determining a location within the building to send the potential building occupant, providing audible or visual signals within the building to guide the potential building occupant to the location, providing instructions to a mobile device of the potential building occupant via a mobile application to guide the potential building occupant to the location.

In some embodiments, the method further includes, in response to the entry decision permitting the potential building occupant to enter the building, determining a testing center within the building to send the potential building occupant, providing audible or visual signals within the building to guide the potential building occupant to the testing center, and, in response to determining that the potential building occupant has tested negative for a contagious disease, providing access to the building for the potential building occupant.

In some embodiments, receiving the indication that the potential building occupant is requesting access into the building includes receiving a request from the potential building occupant via a mobile application to enter the building.

Another implementation of the present disclosure is a controller for providing access into a building. The controller includes a processing circuit including one or more processors and memory, the memory storing instructions that, when executed by the one or more processors, cause the one or more processors to perform operations. The operations include receiving an indication that a potential building occupant is requesting access into the building, providing input data into a probabilistic model, the input data including current health data of the potential building occupant obtained in response to receiving the indication, analyzing, via the probabilistic model, relationships between a plurality of variables within the probabilistic model to determine an entry decision for the potential building occupant, each of the plurality of variables are representative of subsets of the input data, and, in response to the entry decision permitting the potential building occupant to enter the building, providing a control signal to a security system to permit access to the building for the potential building occupant.

In some embodiments, analyzing the relationships between the plurality of variables within the probabilistic model includes determining the subsets of the input data and dependencies between the subsets of the input data, wherein the plurality of variables represent the subsets of the input data and the relationships between the plurality of variables represent the dependencies between the subsets of the input data, determining a joint probability distribution between two or more of the plurality of variables, using the joint probability distribution to determine a probability of the potential building occupant having an infectious disease, and determining the entry decision for the potential building occupant.

In some embodiments, the input data further includes infectious risk data and profile data from a profile associated with the potential building occupant. In some embodiments, the subsets of the input data include at least one of local infection rate, contact tracing status, vaccination status, and temperature.

In some embodiments, the probabilistic model is a Bayesian network model. In some embodiments, the plurality of variables are each weighted based on a likelihood that each of the plurality of variables would affect a probability of the potential building occupant having an infectious disease.

In some embodiments, the processing circuit is further configured to, in response to the entry decision permitting the potential building occupant to enter the building, determine a location within the building to send the potential building occupant, provide audible or visual signals within the building to guide the potential building occupant to the location, provide instructions to a mobile device of the potential building occupant via a mobile application to guide the potential building occupant to the location.

In some embodiments, the processing circuit is further configured to, in response to the entry decision permitting the potential building occupant to enter the building, determine a testing center within the building to send the potential building occupant, provide audible or visual signals within the building to guide the potential building occupant to the testing center, and, in response to determining that the potential building occupant has tested negative for a contagious disease, provide access to the building for the potential building occupant.

In some embodiments, receiving the indication that the potential building occupant is requesting access into the building includes receiving a request from the potential building occupant via a mobile application to enter the building.

Another implementation of the present disclosure is one or more non-transitory computer readable media having instructions stored thereon that, when executed by the one or more processors, cause the one or more processors to implement operations. The operations include receiving an indication that a potential building occupant is requesting access into the building, providing input data into a probabilistic model, the input data including current health data of the potential building occupant obtained in response to receiving the indication. The operations include analyzing, via the probabilistic model, relationships between a plurality of variables within the probabilistic model to determine an entry decision for the potential building occupant, each of the plurality of variables are representative of subsets of the input data. The operations include, in response to the entry decision permitting the potential building occupant to enter the building, providing a control signal to a security system to permit access to the building for the potential building occupant, determining a location within the building to send the potential building occupant, and providing audible or visual signals within the building to guide the potential building occupant to the location.

In some embodiments, analyzing the relationships between the plurality of variables within the probabilistic model includes determining the subsets of the input data and dependencies between the subsets of the input data, the plurality of variables represent the subsets of the input data and the relationships between the plurality of variables represent the dependencies between the subsets of the input data, determining a joint probability distribution between two or more of the plurality of variables, using the joint probability distribution to determine a probability of the potential building occupant having an infectious disease, and determining the entry decision for the potential building occupant.

In some embodiments, the input data further includes infectious risk data and profile data from a profile associated with the potential building occupant and the subsets of the input data include at least one of local infection rate, contact tracing status, vaccination status, and temperature.

In some embodiments, the probabilistic model is a Bayesian network model and the plurality of variables are each weighted based on a likelihood that each of the plurality of variables would affect a probability of the potential building occupant having an infectious disease.

In some embodiments, the one or more processors are further configured to, in response to the entry decision permitting the potential building occupant to enter the building, determining a testing center within the building to send the potential building occupant, providing audible or visual signals within the building to guide the potential building occupant to the testing center, and, in response to determining that the potential building occupant has tested negative for a contagious disease, providing access to the building for the potential building occupant.

In some embodiments, receiving the indication that the potential building occupant is requesting access into the building includes receiving a request from the potential building occupant via a mobile application to enter the building.

DETAILED DESCRIPTION

Overview

Figure 1:
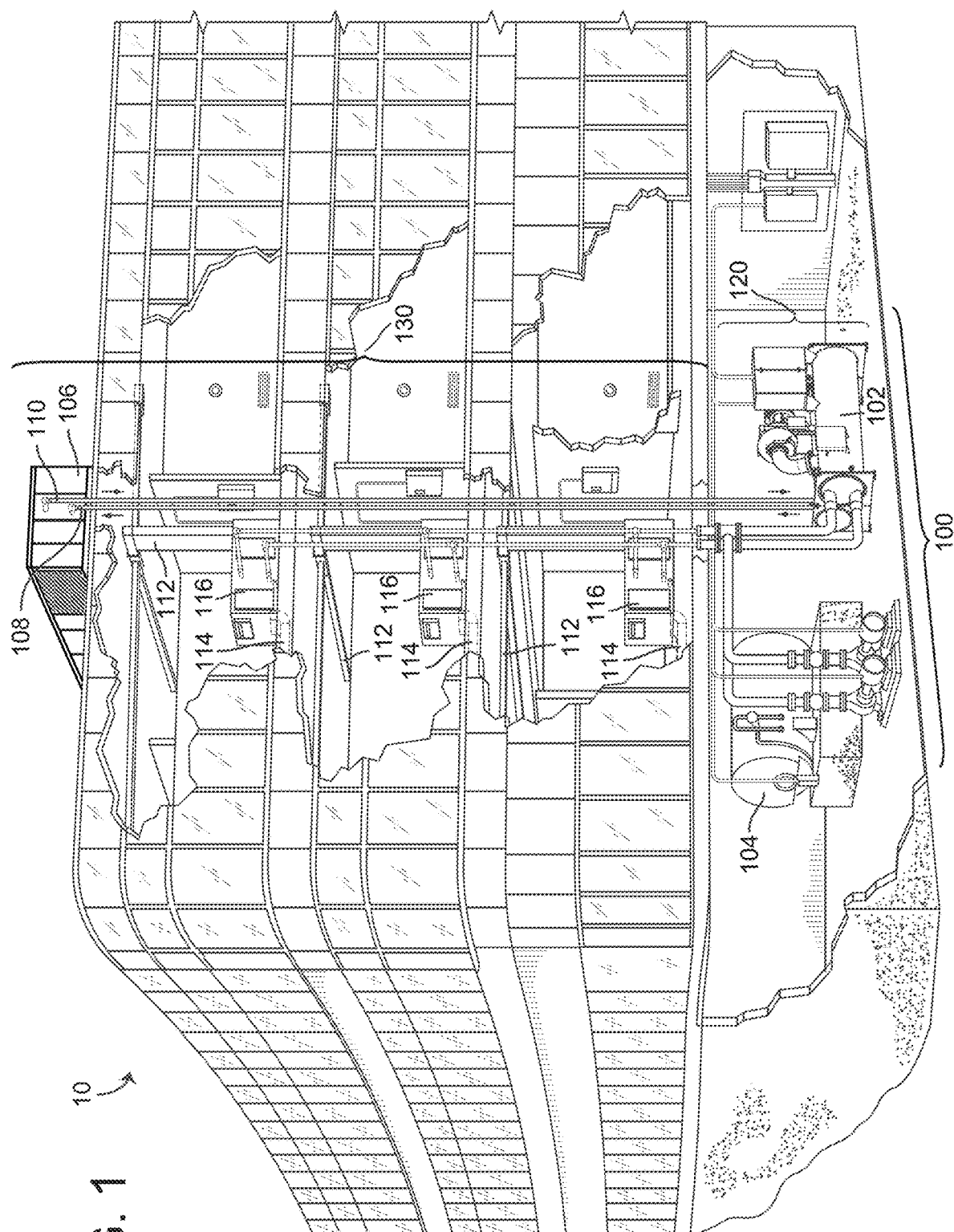
FIG. 1 is a drawing of a building equipped with a HVAC system, according to an exemplary embodiment.

Referring generally to the FIGURES, systems and methods for providing safe and efficient access throughout a building for potential building occupants (PBOs) are shown, according to some embodiments. To mitigate health risks in an environment, such as mitigating the spread of an infectious disease (e.g., COVID-19, etc.), it can be desirable for a building management system (BMS) to evaluate and manage requests of PBOs to enter a building, and to have the BMS make entry decisions based on infectious risk data, environmental data, and/or current health data of the PBO.

In some embodiments, the BMS employs an access control system (ACS) that is configured to dynamically determine entry decisions for PBOs. This can include providing infectious risk data (e.g., local infection rate, current COVID-19 standards, etc.), environmental data (e.g., weather, method of commute, etc.), and current health data of the PBO (e.g., vaccination status, contract trancing status, temperature, etc.) to a model within the ACS that is configured to make a dynamic entry decision on whether to grant access to the building for the PBO. For example, the model can be a probabilistic model, such as a Bayesian network model, that uses relationships between different variables (e.g., temperature, vaccination status, etc.) to make an inference about the safety risk of granting access to the user (e.g., inferring the chances of the PBO having COVID-19, etc.). The model may be trained on system data, where data may be binary, with probability scores attached to each state. Additionally, some of the data may be pre-processed or pre-classified by a system admin, who manually adjusts the weighting of relationships in the system. For example, certain employee roles may be considered to carry a higher infection risk, which may then increase the likelihood that an employee is sent for a test. Advantageously, this technique can provide faster and more accurate health decisions by considering multiple health variables and the relationships thereof.

In some embodiments, the ACS may be configured to also or separately provide dynamic routing for PBOs from when they have been granted access into the building to their desired location, and anywhere in between. For example, a PBO is granted access into the building after the ACS makes an entry decision that the PBO is safely allowed to enter the building (e.g., based on decisions made by a probabilistic model, etc.). The ACS is also aware of where the PBO needs to go within the building (e.g., the PBO is going to their office and the ACS knows their office location, the PBO requested to go to a location via a mobile application connected to the ACS, etc.), and provides A/V signals to safely guide the PBO to the location. These can include light signals (e.g., illuminating arrows on the floor to guide the PBO, etc.), audio signals (e.g., verbal instructions provided over an intercom, etc.), and/or video signals (e.g., a video is provided to the mobile device of the PBO via a mobile application guiding the PBO to the location, etc.). Advantageously, this technique can provide a contactless routing system, which can increase social distancing to reduce risks of infection among building occupants.

Building Site

Referring now to FIG. 1, a perspective view of a building 10 is shown. Building 10 is served by a building management system (BMS). A BMS is, in general, a system of devices configured to control, monitor, and manage equipment in or around a building or building area. A BMS can include, for example, a HVAC system, a security system, a lighting system, a fire alerting system, any other system that is capable of managing building functions or devices, or any combination thereof.

The BMS that serves building 10 includes a HVAC system 100. HVAC system 100 may include a plurality of HVAC devices (e.g., heaters, chillers, air handling units, pumps, fans, thermal energy storage, etc.) configured to provide heating, cooling, ventilation, or other services for building 10. For example, HVAC system 100 is shown to include a waterside system 120 and an airside system 130. Waterside system 120 may provide a heated or chilled fluid to an air handling unit of airside system 130. Airside system 130 may use the heated or chilled fluid to heat or cool an airflow provided to building 10. In some embodiments, waterside system 120 is replaced with a central energy plant such as central plant 200, described with reference to FIG. 2.

Still referring to FIG. 1, HVAC system 100 is shown to include a chiller 102, a boiler 104, and a rooftop air handling unit (AHU) 106. Waterside system 120 may use boiler 104 and chiller 102 to heat or cool a working fluid (e.g., water, glycol, etc.) and may circulate the working fluid to AHU 106. In various embodiments, the HVAC devices of waterside system 120 may be located in or around building 10 (as shown in FIG. 1) or at an offsite location such as a central plant (e.g., a chiller plant, a steam plant, a heat plant, etc.). The working fluid may be heated in boiler 104 or cooled in chiller 102, depending on whether heating or cooling is required in building 10. Boiler 104 may add heat to the circulated fluid, for example, by burning a combustible material (e.g., natural gas) or using an electric heating element. Chiller 102 may place the circulated fluid in a heat exchange relationship with another fluid (e.g., a refrigerant) in a heat exchanger (e.g., an evaporator) to absorb heat from the circulated fluid. The working fluid from chiller 102 and/or boiler 104 may be transported to AHU 106 via piping 108.

AHU 106 may place the working fluid in a heat exchange relationship with an airflow passing through AHU 106 (e.g., via one or more stages of cooling coils and/or heating coils). The airflow may be, for example, outside air, return air from within building 10, or a combination of both. AHU 106 may transfer heat between the airflow and the working fluid to provide heating or cooling for the airflow. For example, AHU 106 may include one or more fans or blowers configured to pass the airflow over or through a heat exchanger containing the working fluid. The working fluid may then return to chiller 102 or boiler 104 via piping 110.

Airside system 130 may deliver the airflow supplied by AHU 106 (i.e., the supply airflow) to building 10 via air supply ducts 112 and may provide return air from building 10 to AHU 106 via air return ducts 114. In some embodiments, airside system 130 includes multiple variable air volume (VAV) units 116. For example, airside system 130 is shown to include a separate VAV unit 116 on each floor or zone of building 10. VAV units 116 may include dampers or other flow control elements that can be operated to control an amount of the supply airflow provided to individual zones of building 10. In other embodiments, airside system 130 delivers the supply airflow into one or more zones of building 10 (e.g., via air supply ducts 112) without using intermediate VAV units 116 or other flow control elements. AHU 106 may include various sensors (e.g., temperature sensors, pressure sensors, etc.) configured to measure attributes of the supply airflow. AHU 106 may receive input from sensors located within AHU 106 and/or within the building zone and may adjust the flow rate, temperature, or other attributes of the supply airflow through AHU 106 to achieve setpoint conditions for the building zone.

Access Control System Overview

Figure 2:
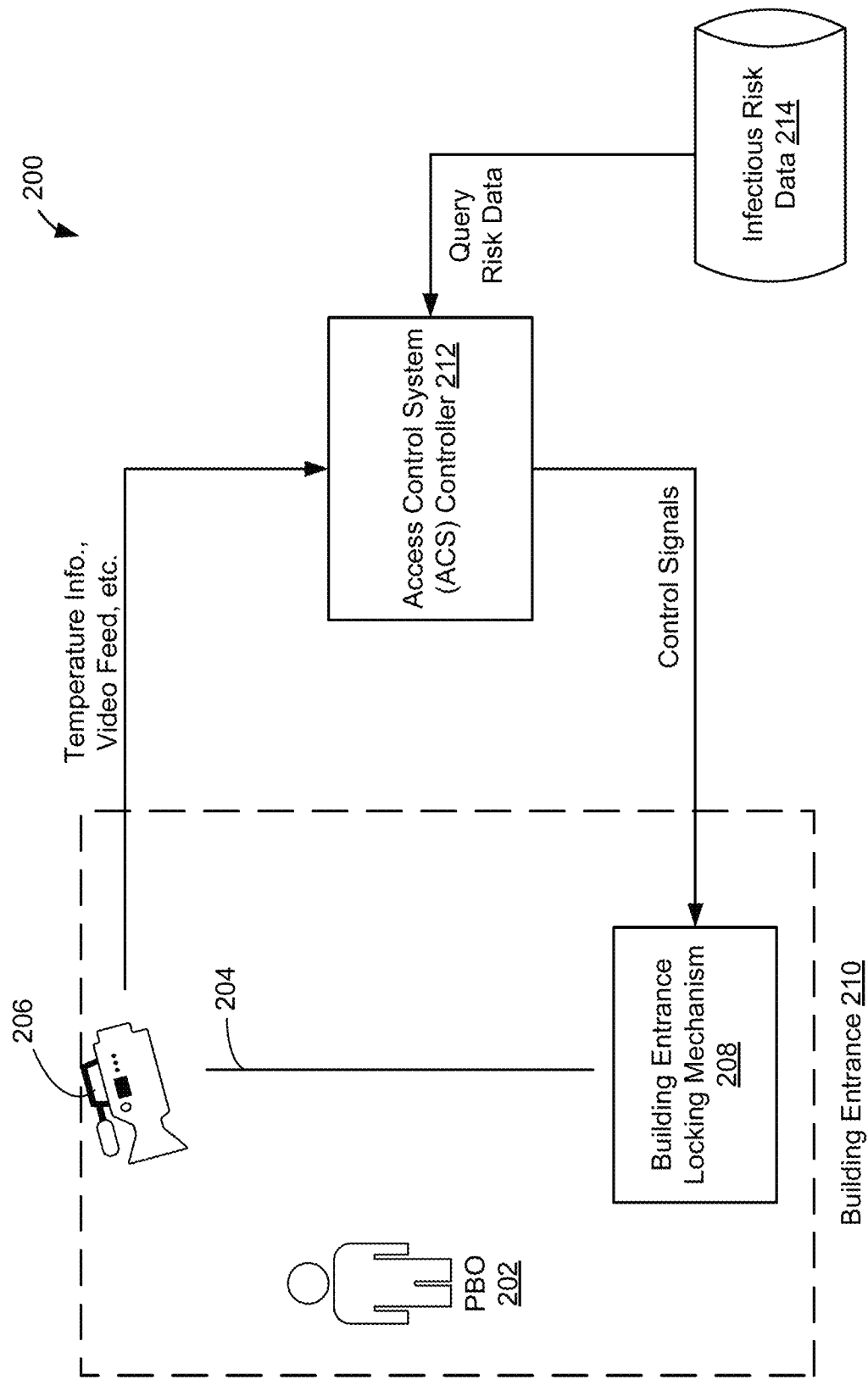
FIG. 2 is a block diagram of an entrance security system for a building, which can be implemented in the building of FIG. 1, according to an exemplary embodiment.

Referring now to FIG. 2, a block diagram of security system 200 is shown, according to some embodiments. System 200 may be implemented within building 10 and may be configured to implement security measures within building 10, such as access to building 10. System 200 is shown to include potential building occupant (PBO) 202, entrance 204, camera subsystem 206, building entrance locking mechanism ("mechanism") 210, access control system (ACS) controller ("controller") 212, and infectious risk data 214.

PBO 202 may be any type of individual entering, or planning to enter, building 10. This can include building employees, previously employed employees, students and/or visitors to building 10. In some embodiments, PBO 202 is attempting to gain access into building 10. For example, PBO 202 contacts controller 212 via a mobile application, and transmits this request to controller 212 via the mobile application. In some embodiments, the mobile application provides updates to PBO 202 on the status of gaining entrance into building 10 and can provide updates/reasons on the decided entry decision.

Camera subsystem 206 may be configured to obtain real-time data of PBO 202 prior, during, and/or after the PBO's request to pass through entrance 204 is received. For example, in response to controller 212 receiving an indication that PBO 202 is requesting accesses through entrance 204, a temperature sensor may obtain the temperature of PBO 202. In some embodiments, subsystem 206 is also configured to provide static images and/or video feed to controller 212 of PBO 202. This may occur when PBO 202 is within range of cameras within subsystem 206, after they have entered building 10 and passed through entrance 204, and any time in between.

In some embodiments, controller 212 is configured employ access control into and/or out of entrance 204 using one or more probabilistic models. In the event of an entry decision indicating that PBO is allowed into building 10, controller 212 may provide control signals to building entrance locking mechanism 208 to allow PBO 202 to enter through entrance 204. This may include opening entrance gates that are typically locked, and permitting the PBO 202 to gain access after a virtual lock is disengaged. In other embodiments, this may include allowing a code on the mobile application of PBO 202 to be received (e.g., scanned, entered, etc.) into a terminal at or near entrance 204 that thereby permits access through entrance 204.

While the systems and methods disclosed herein are generally referring to probabilistic models (e.g., graphical models, probabilistic graphical models, structured probabilistic model, undirected graphical models, cyclic directed graphical models, etc.), and in particular Bayesian network models, these are merely meant to be exemplary and should not be considered limiting. Other types of dynamic decision-making tools can be used and/or implemented, such as deterministic models, statistical models, deep learning models, and other models implanting types of artificial intelligence. It is worth noting that any and all data taken, recorded, and/or determined during the processes disclosed herein can be stored and used for future analytics.

While not shown in FIG. 2, controller 212 may also be configured to provide control signals to audio, visual, or electrical subsystems that can be configured to guide PBO 202 (i.e., after gaining access to building 10 through entrance 204) to a desired (e.g., per a request from PBO 202, etc.) and/or suggested (e.g., decided by controller 212, etc.) location within building 10. In some embodiments, controller 212 can also be configured to guide PBO 202 (i.e., after being denied access to building 10) to a location that mitigates subsequent health risks, such as a nearby testing location or a hospital. In some embodiments, controller 212 is configured to perform both types of guiding processes.

Controller 212 may be configured to receive the temperature and/or video data from subsystem 206, along with a series of other data points. These data points may be provided by the PBO 202 (e.g., vaccination status, current feelings of sickness, etc.) and/or may be queried from a profile of the PBO 202 in a database coupled controller 212. For example, controller 212 includes a database of profiles corresponding to employees working at building 10. Controller 212 queries the profile database to determine a variety of information associated with PBO 202, such as their vaccination history, preferred method of commuting to work, contact tracing information, COVID-19 status, and health information.

While the systems and methods disclosed herein are generally referring to the entrance of building 10, any location in which access may be barred by security measures can implement the systems and methods disclosed herein. For example, an entrance into a large space (e.g., cafeteria, auditorium, etc.), or a section of a building that requires stricter security protocols. Controller 212 is described in greater detail below with reference to FIG. 3.

Figure 3:
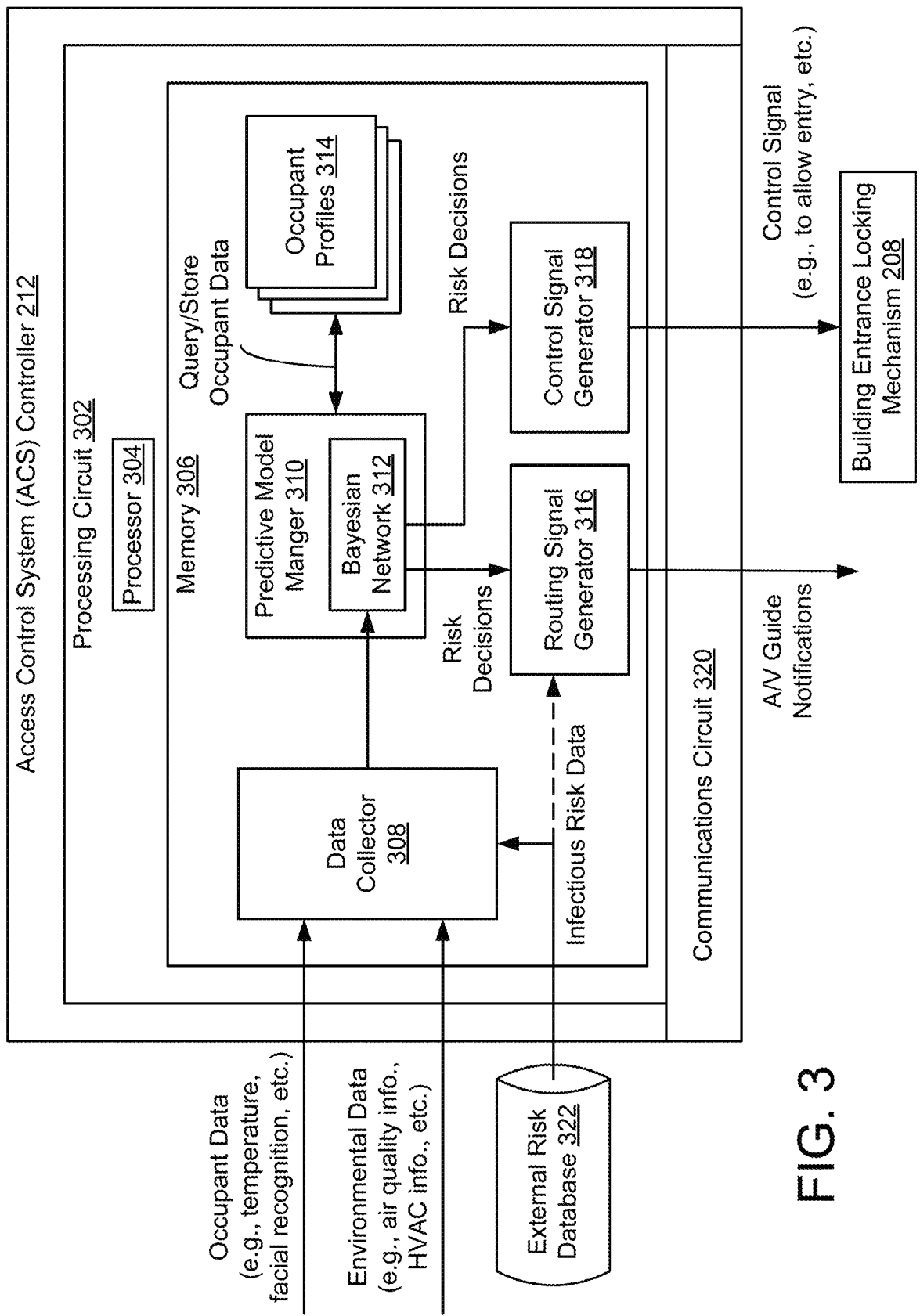
FIG. 3 is a block diagram of an access control system (ACS) controller, which can be implemented in the entrance security system of FIG. 2, according to an exemplary embodiment.

Referring now to FIG. 3, detailed block diagram of controller 212 is shown, according to some embodiments. Controller 212 is shown to includes communications interface 320 and processing circuit 302 including processor 304 and memory 306. Processing circuit 302 can be communicably connected to communications interface 320 such that processing circuit 302 and the various components thereof can send and receive data via communications interface 320. Processor 304 can be implemented as a general purpose processor, an application specific integrated circuit (ASIC), one or more field programmable gate arrays (FPGAs), a group of processing components, or other suitable electronic processing components.

Communications interface 320 can be or include wired or wireless communications interfaces (e.g., jacks, antennas, transmitters, receivers, transceivers, wire terminals, etc.) for conducting data communications. In various embodiments, communications via communications interface 320 can be direct (e.g., local wired or wireless communications) or via a communications network (e.g., a WAN, the Internet, a cellular network, etc.). For example, communications interface can include an Ethernet card and port for sending and receiving data via an Ethernet-based communications link or network. In another example, communications interface 320 can include a Wi-Fi transceiver for communicating via a wireless communications network. In another example, communications interface 320 can include cellular or mobile phone communications transceivers.

Memory 306 (e.g., memory, memory unit, storage device, etc.) can include one or more devices (e.g., RAM, ROM, Flash memory, hard disk storage, etc.) for storing data and/or computer code for completing or facilitating the various processes, layers and modules described in the present disclosure. Memory 708 can be or include volatile memory or non-volatile memory. Memory 306 can include database components, object code components, script components, or any other type of information structure for supporting the various activities and information structures described in the present disclosure. According to an example embodiment, memory 306 is communicably connected to processor 304 via processing circuit 302 and includes computer code for executing (e.g., by processing circuit 302 and/or processor 304) one or more processes described herein.

In some embodiments, controller 212 is implemented within a single computer (e.g., one server, one housing, etc.). In various other embodiments controller 212 can be distributed across multiple servers or computers (e.g., that can exist in distributed locations). FIG. 3 is shown to include controller 212, external risk database 322, and mechanism 208, and memory 306 is shown to include data collector 308, predictive model 310 including Bayesian network 312, occupant profiles 314, routing signal generator 316, and control signal generator 318.

Data collector 308 may be configured to receive any and all information provided to controller 212. While data collector 308 is generally collecting data that includes some or all of health data of PBO 202, infectious risk data, and environmental data, other data and/or data sets can be considered and analyzed to perform the processes herein. Data collector 308 may be configured to receive several data sets and provide the data predictive model manager 310. In some embodiments, as shown in FIG. 3, manager 310 may be configured to query and/or store data in occupant profiles 314 without passing through data collector 308.

Data collector 308 may be configured to receive occupant data or current health data associated with one or more PBO 202. In some embodiments, current health data of PBO 202 includes any data or information pertaining the past or present health of the PBO 202. For example, the current health data of PBO 202 includes temperature, current vaccination status, previous vaccination information, feelings of sickness, tests statuses, self-reporting information, method of commute to building 10, contact tracing information, or any combination thereof.

Data collector 308 may also receive infectious risk data, which can include specific information about present diseases or pandemics. For example, the infectious risk data can include updated reports/mandates/protocols from government bodies pertaining to COVID-19, local infection rates, local guidelines, company guidelines, social distancing requirements, updates relating to COVID-19 studies, updated testing protocols, or any combination thereof. Data collector 308 may also receive environmental data, which can include data affecting the spread of infectious diseases. For example, the environmental data can include local weather data, wind speeds, building air filtration information (e.g., indicating how airborne pathogens would travel within building 10), risk levels within building 10, or any combination thereof.

Predictive model manager 310 may be configured to receive data from data collector 308 as inputs into a model. In some embodiments, the model is a probabilistic model that includes Bayesian network 312 and is configured to determine a likelihood of risk for PBO 202 entering building 10. Manager 310 may implement a model that uses the different data subsets (e.g., local infection rate, COVID status, contact tracing, etc.) as variables within the model, and mathematically determines their conditional dependencies on one another based on their relationships. This can allow manager 310 to compute the probabilities of certain scenarios. In the embodiments described herein, manager 310 may be configured to compute the probability of PBO 202 having an infectious disease, or computing the probability of PBO 202 being a risk to others if allowed in building 10. The methods in which manager 310 may use these variables and the relationships thereof to compute probabilities and make decisions is described in greater detail below with reference to FIG. 4.

Routing signal generator 316 may be configured to receive the risk decisions or other decisions from manager 310 and provide, if necessary, guidance to a decided location for PBO 202. For example, generator 316 receives an indication that that PBO 202 is allowed to enter building 10 and is granted full access. Routing signal generator 316 then generates audible and/or visual signals to guide PBO 202 to their office. While PBO 202 may know the path to their office, the guidance may guide them on a path that maximizes social distancing to mitigate health risks.

In another example, routing generator 316 receives an indication that PBO 202 is allowed to enter building 10, but needs to be tested in the in-building testing center prior to being granted full access throughout building 10. As such, generator 316 generates audible and/or visual signals to guide PBO 202 to the in-building testing center. Controller 212 may then receive an indication whether PBO 202 has passed an infectious disease test and, in response to determining that PBO 202 does not have the infectious disease, proceed with granting them full access to building 10.

Control signal generator 318 may be configured to receive risk decisions from manager 310 and to generate control signals to unlock mechanism 208 in response to manager 310 determining that PBO 202 should be allowed to enter building 10. In some embodiments, control signal generator electronically unlocks a gate and/or lock at or near entrance 204. In other embodiments, control signal generator 318 may provide a wireless signal to a mobile device of PBO 202 via a mobile application, which can unlock/generate an access code (e.g., QR code, numerical code, security code, etc.). Then, PBO 202 may use the mobile device to access entrance 204.

Access Control Processes Using Probabilistic Modeling

Figure 4A:
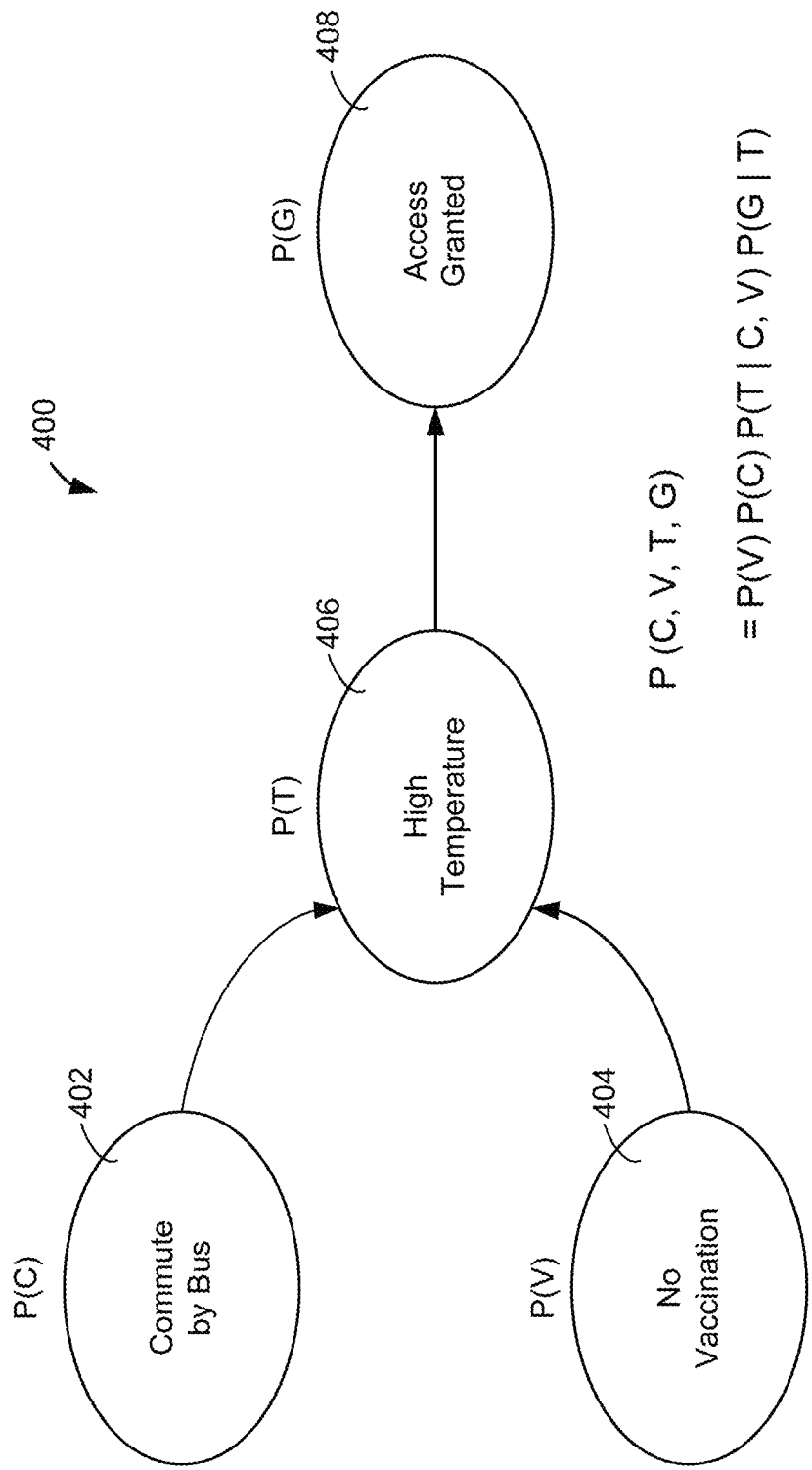
FIG. 4A is a simplified diagram of a probabilistic network for making entry decisions, which can be implemented in the ACS controller of FIG. 3, according to an exemplary embodiment.

Referring now to FIG. 4A, a diagram 400 of a network model is shown, according to some embodiments. FIG. 4A is shown to include "commute by bus" node 402, "no vaccination" node 404, "high temperature" node 406, and "access granted" node 408, along with edges connecting the multiple nodes. In some embodiments, diagram 400 is graphical model with multiple nodes 402-408, and edges (i.e., the lines connecting the nodes). The graphical model me be representation of a Bayesian network, where the conditional probability of node 408 may be determined based on parent nodes (i.e., node 406) or grand-parent nodes (i.e., nodes 402, 404). For the following equations described herein, random variables may be referred to in capital letters (e.g., "A"), while values of variables may be referred to in lowercase letters (e.g., The definition of conditional probability may be defined as the following:

$$P(a \mid b) = \frac{P(a, b)}{P(b)} \qquad \text{Eq. (1)}$$

which states that the probability of a given b is equal to the joint probability of a and b, divided by the probability of b. For example (not shown in FIG. 4A), a is the event that PBO 202 has COVID-19, and b is the event that PBO 202 has a temperature greater than 99°. Therefore, Eq. (1) would state that the probability of PBO 202 having COVID-19, given the fact that PBO 202 has a temperature greater than 99°, is equal to the probability of that PBO 202 has COVID-19 ("a") and has a temperature greater than 99° ("b"), divided by the probability that PBO 202 has a temperature greater than 99° ("b").

Similarly, the probability of b, given a, may be defined using Bayes Rule:

$$P(b \mid a) = \frac{P(a, b)P(b)}{P(a)} \qquad \text{Eq. (2)}$$

Where the probability of b given a is equal to the probability of a and b times the probability of b, divided by the probability of a. Additionally, the joint probability distribution of nodes 402-408 within diagram 400 may be defined as:

$$P(C,V,T,G)=P(V)P(C)P(T|C,V)P(G|T) \quad \text{Eq. (3)}$$

Where the joint probability P(C, V, T, G) is equal to the probability of V times the probability of C times the probability of T given C or V times the probability of G given T. In some embodiments, controller 212 may use this Bayesian network (e.g., diagram 400) to make probabilistic determinations.

For example, controller 212 may want to determine (e.g., perform an inference of) the probability of access being granted for PBO 202 (e.g., node 408), given that PBO 202 commuted by bus (e.g., node 402). This may be defined as:

$$P(C\mid G) = \sum_T \sum_V \frac{P(c, v, t, g)}{P(g)} \quad \text{Eq. (4)}$$

Which can be simplified to:

$$P(c\mid g) \propto \sum_t \sum_v P(c)P(v)P(t\mid c, v)P(g\mid T) \quad \text{Eq. (5)}$$

Where the unconsidered variables T, V are summed, and the probability of access being granted is divided out for each of the probabilities for each node 402-408. Eq. (5) may be calculated by controller 212 to determine a probability of access being granted to PBO 202 given PBO 202 commuting by bus. If the determined probability is over a predetermined threshold (e.g., 5 percent, 10 percent, 20 percent, 50 percent, etc.), controller 212 may determine that that PBO 202 is required to take a test for an infectious disease and test negative prior to entering building 10.

It is worth noting that the variables used in diagram 400 are merely meant to be exemplary and should not be considered limiting. For example, node 408 may be replaced with "positive for COVID-19" and controller 212 wants to determine the probability of PBO 202 testing positive for COVID-19 give PBO not being vaccinated (e.g., P(V)). Multiple other nodes may considered, as shown in greater detail with reference to FIG. 4B.

Figure 4B:
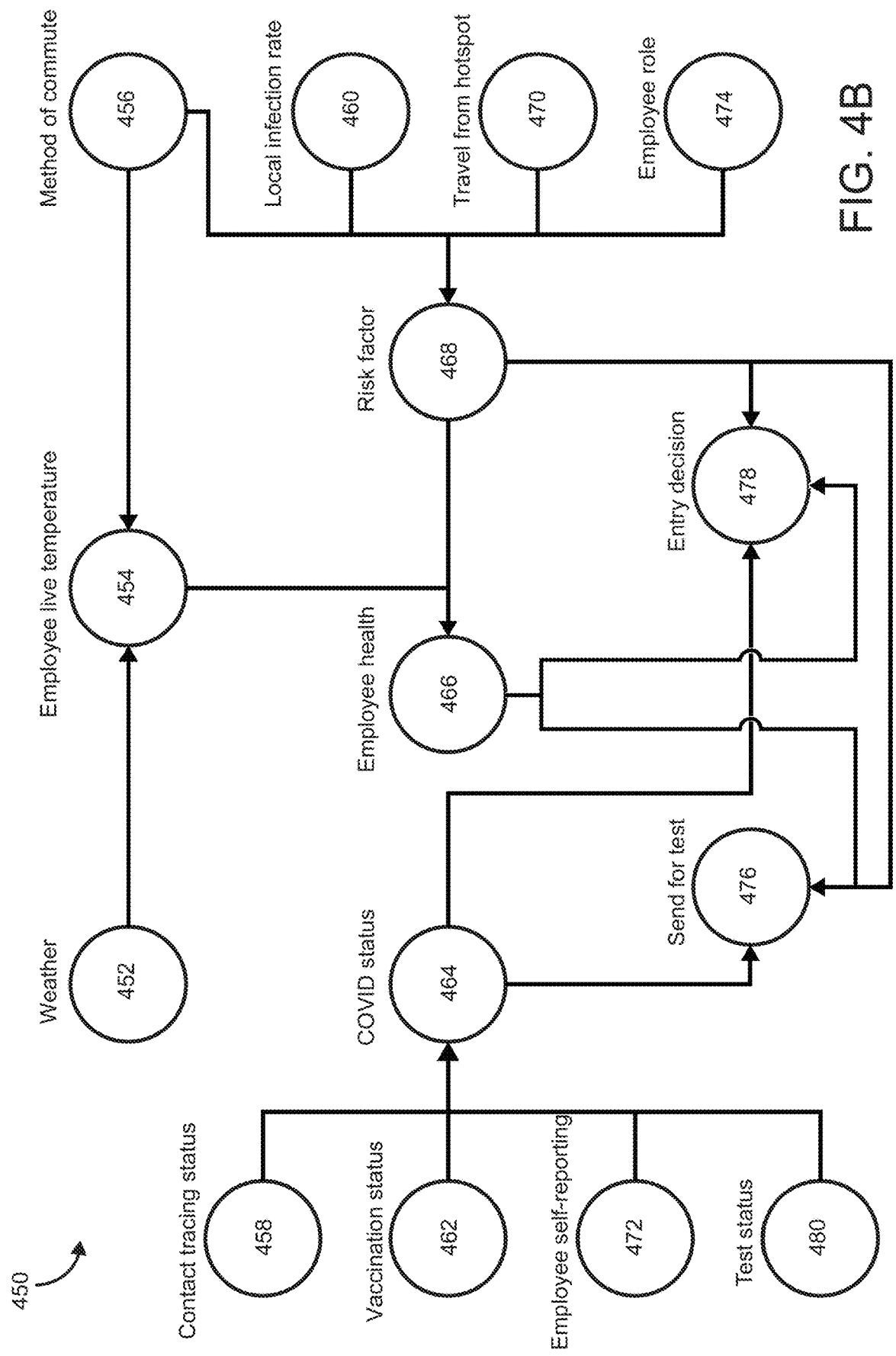
FIG. 4B is a detailed diagram of a probabilistic network for making entry decisions, which can be implemented in the ACS controller of FIG. 3, according to an exemplary embodiment.

Referring now to FIG. 4B, a detailed diagram 450 of a network model is shown, according to some embodiments. Diagram 450 may be part of Bayesian network model 312 of controller 212, and is configured to make probability decisions for multiple variables. These variables may be based on a set of assumptions regarding likely factors that would affect PBO 202 likelihood of having COVID-19 (e.g., their temperature, as represented by node 454), according to some embodiments. As mentioned above, the connecting lines (e.g., edges) represent the relationships between the variables (e.g., nodes).

In some embodiments, rules based on these variables are represented in Bayesian network model 312 as nodes contributing to joint probability calculations that score target nodes, whether the user should be admitted, and/or sent for a test (represented by node) 476. For example, a high local infection rate 460 can dynamically increase the likelihood that an employee with a higher than average temperature is instructed to go to a testing center for a test. Bayesian network model 312 may be trained on previous system data (e.g., where data may be binary, etc.) with probability scores attached to each state. Additionally, some of the data may be pre-processed or pre-classified by a system administrator, who manually adjusts the weighting of relationships in the system. For example, certain employee roles may be considered to carry a higher infection risk, which may then increase the likelihood that an employee is sent for a test at a testing center.

In some embodiments, entry decision node 478 represents the possible entry decisions, as outlined above. Three other variables may represent the primary sources of data in the in the system as they represent the main sources of data for the entry decision node 478. These include the COVID status node 464, the employee health node 466 and the risk factor node 468, according to some embodiments. Based on the accumulated data provided to these variables, the risk is assessed, and an entry decision may be calculated. Multiple examples of this process are outlined below.

In one non-limiting example, a self-reporting health application (represented by node 472) is completed by all employees may be used to flag infection risks. An employee that reports multiple symptoms of an infectious disease on the app may prompt the system to send the employee for an on-site test. The employee takes a test and the test results prove negative. Based on these results, the system deems the employee a low infection risk and allows entry.

In another non-limiting example, live thermal cameras in the entrance area of a building can report the temperature of building entrants. Tracking software can then associate that temperature with the building entrant and use this data to profile the health of the building entrant. The weighting of this data can also be altered depending on other data sources, such as the outside air temperature, the method of commute of the building entrant, the employee role etc. For example, if the outside air temperature is cold, but the local infection rate is high and the building entrant is reporting a high temperature reading, then the system may deny entry or send the building entrant for a test.

In another non-limiting example, an employee may return to his office building after a business trip to a country that has a high infection rate. The system admin has implemented a company policy that all employees returning from 'infection hotspots' abroad need to work from home for two weeks. The system denies entry to the employee until the work from home period expires.

In another non-limiting example, PBO 202 has been vaccinated against COVID-19 through a national vaccination program. The building entrant validates the status of their vaccination 106 through an app on their phone at an entry point. The system may connect to a national database to verify the presented data, if available. The system notes that the vaccination occurred nine months previously. The user admin has configured the system so that only building entrants vaccinated in the previous six months are allowed entry when the local infection rate is high. The local infection rate 105 is this instance is low. The system deems the building entrant a low risk and allows entry.

In another non-limiting example, two employees of a company live in the same area and both commute to building 10 via a bus (represented by node 456). One employee reports as positive for an infectious disease through the company's self-reporting health application. The other employee is sent for a test by the controller 212, for the next week, every morning. Even though the second employee does not exhibit any other symptoms, controller 212 flags a risk due to their shared method of commute and the locations of their home address.

In another non-limiting example, a student in a school tests positive for an infectious disease after being sent for a test by the access control system. All other students in the same class as this student (employee role could be adapted for different settings) are sent for a test upon arrival by the access control system. Two other students test positive and are denied entry. All other students test negative and are allowed entry.

Using a probabilistic model, such as Bayesian network model 312, to make probabilistic determinations may provide helpful decision making for a variety of situations. Multiple scenarios are shown below for reference.

In one non-limiting example, thermal cameras may record a high temperature for an employee working in a warehouse. The local infection rate of a disease, which includes a high temperature as a symptom, is 100 cases per day. An ordinary decision tree may feature a tree, with a pre-defined startpoint and endpoint, and yes/no decisions at each variable, such as the following: role→temperature→infection rate→Symptoms→Access decision. However, a Bayesian network may provide for a dynamic relationship between the variables and contributes to a joint probability calculation. For example, a certain employee role, such as warehouse worker, may decrease the likelihood of being sent for a test as a higher temperature may be considered normal. In the same instance, a higher local infection rate may increase the likelihood of being sent for a test as a warehouse worker may have higher interaction with delivery personnel. In this manner the weighting of relationships between multiple variables is calculated across the network and a comprehensive joint probability decision is calculated. This also allows for a more nuanced and informed access decision.

In another non-limiting example, thermal cameras record a high temperature in an employee. The method of commute of the employee is bicycle. The weighting of the temperature node is decreased due to the relationship with the employee's method of commute, therefore access is granted.

In another non-limiting example, an employee has been vaccinated as part of a government vaccination program. The employee has also been tested for a disease, such as COVID-19, two days previously. The employee is reporting symptoms such as fever and sore throat, which are typically deemed symptoms of concern. However, other nodes in the Bayesian network Vaccination status, test status and perhaps local infection rate, dynamically decrease the weighting of the Employee self-reporting node, and so despite symptoms, the access system allows entry.

Contactless Routing Diagrams

Figure 5:
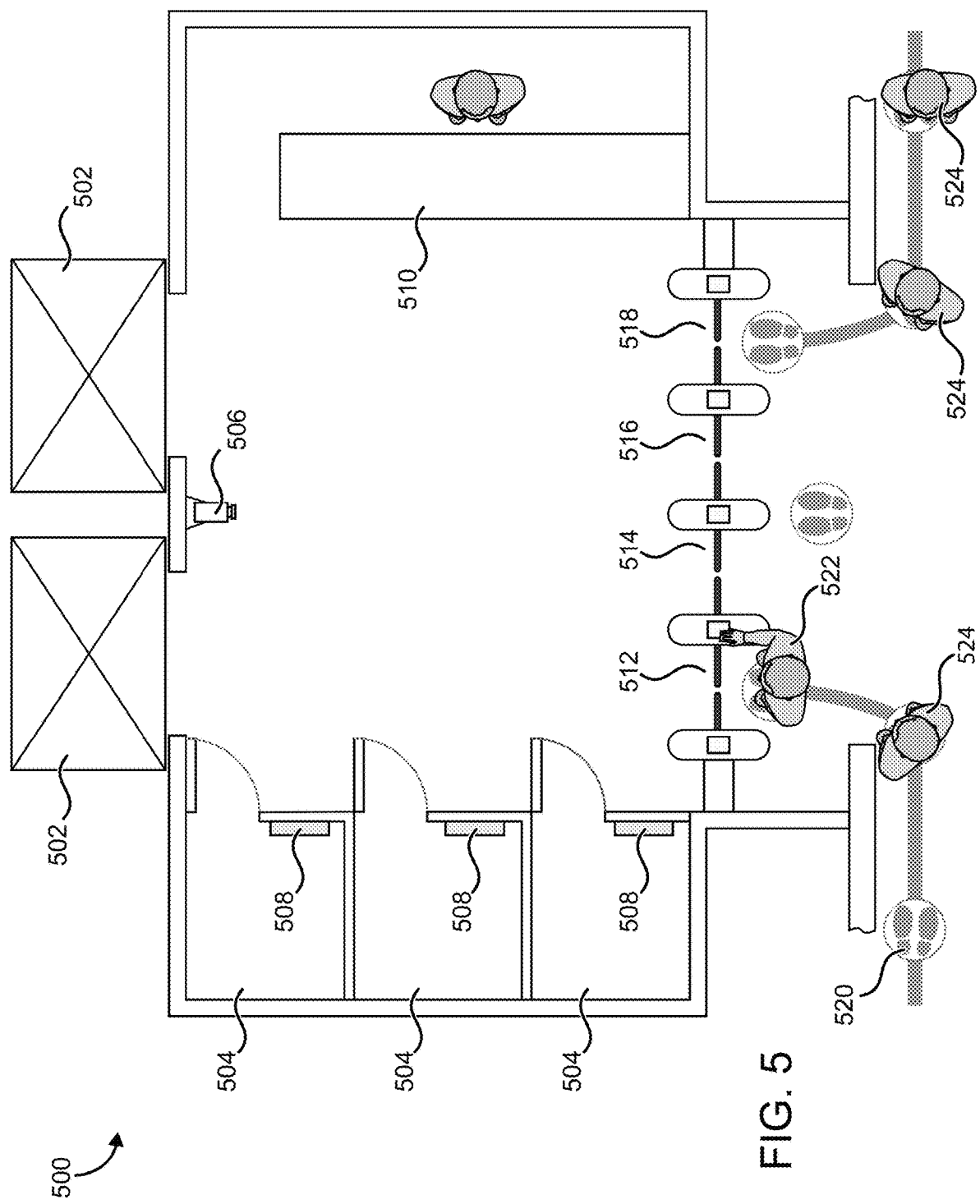
FIG. 5 is a diagram of an entrance gate security system providing selective entry decisions for potential building occupants, which can be implemented in the system of FIG. 2, according to some embodiments.
Figure 6:
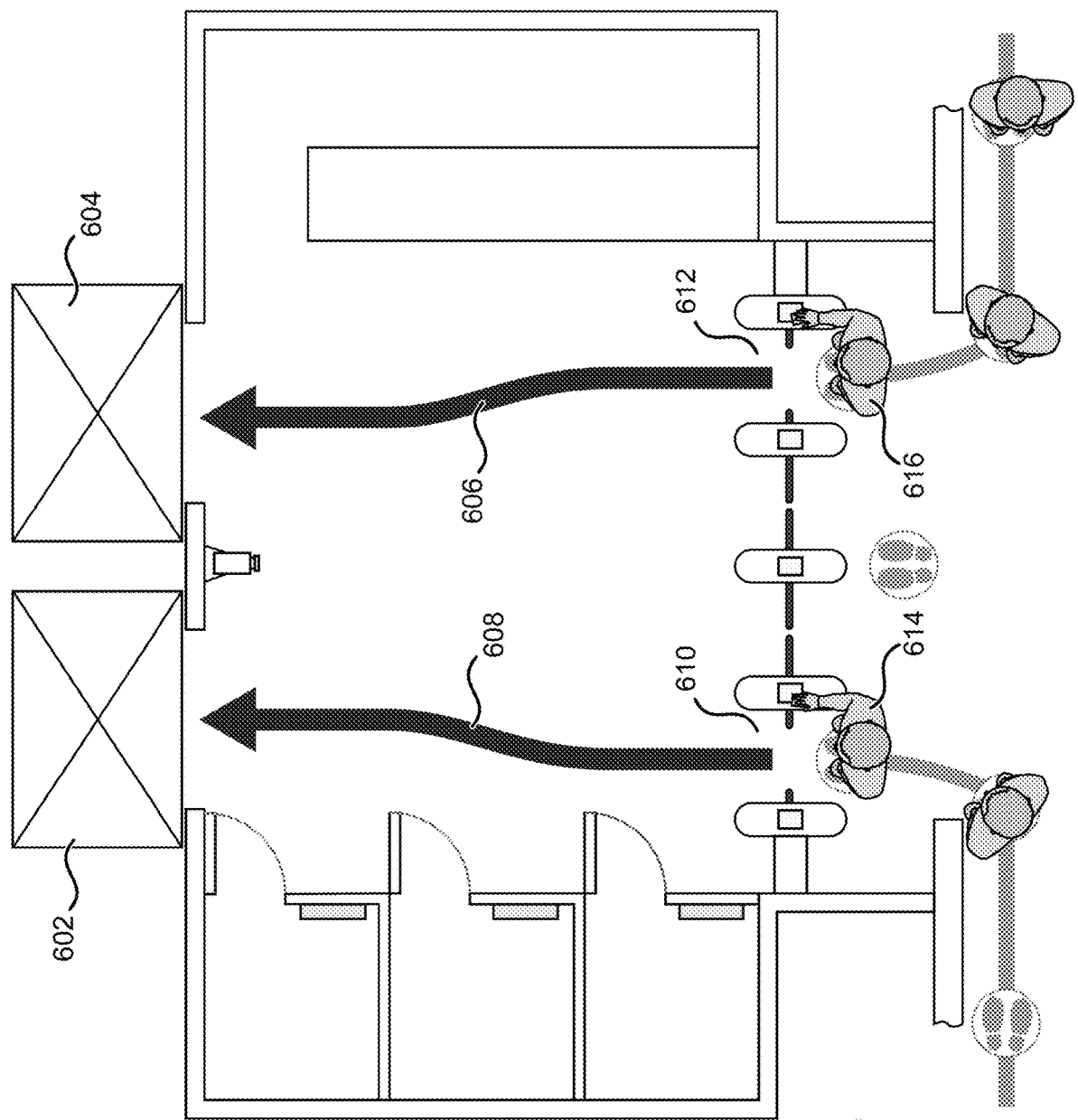
FIG. 6 is a diagram of a security system using contactless routing, which can be implemented in the system of FIG. 2, according to some embodiments.

Referring generally to FIGS. 5-9, diagrams of an entrance lobby of building 10 with controller 212 performing contactless routing for PBO's is shown, according to some embodiments. FIGS. 5-9 and the processes shown therein may be performed separately or together, either partially or entirely, by controller 212. It is worth noting that while the various digital displays, elevators, cameras, desks, pathways, and other components may be described using different reference numbers, the components may be partially or entirely similar across the multiple diagrams. For example, turnstiles 512-518 as shown in FIG. 5 may be substantially similar to turnstiles 610, 612 as shown in FIG. 6.

Referring now to FIG. 5, a diagram 500 of an entrance lobby to building 10 is shown, according to some embodiments. Diagram 500 is shown to include access control turnstiles 512-518, reception desk 510, waiting rooms 504, digital displays 508, elevators 502, and thermal imaging camera 506. A person, for example person 522, may attempt to gain entry by presenting their ID card at a turnstile, for example turnstile 506. People 524 may queue to gain access to turnstiles 512-518. Floor markers, such as floor marker 520, may be used to indicate where people should stand in the queue to maintain appropriate social distancing. Turnstiles 512-518 may also be assigned specific purposes to maintain appropriate social distancing. For example, turnstiles 512 and 518 may be used for entry into the building, while turnstiles 514 and 516 may be use for exit from the building, or for people who are not required to queue, such as people making deliveries.

Referring now to FIG. 6, operation of controller 212 when entry is permitted for PBOs is shown, according to some embodiments. Persons 614 and 616 present their ID cards to turnstiles 610 and 612 respectively. ACS 200 can access their individual risks and grants access to both. Person 614 is directed to elevator 602, which enables them to follow direct route 608. Similarly, person 612 is directed to elevator 604, which enables them to follow direct route 606. In both cases the doors of elevators 602 and 604 may open automatically to enable frictionless entry.

Figure 7:
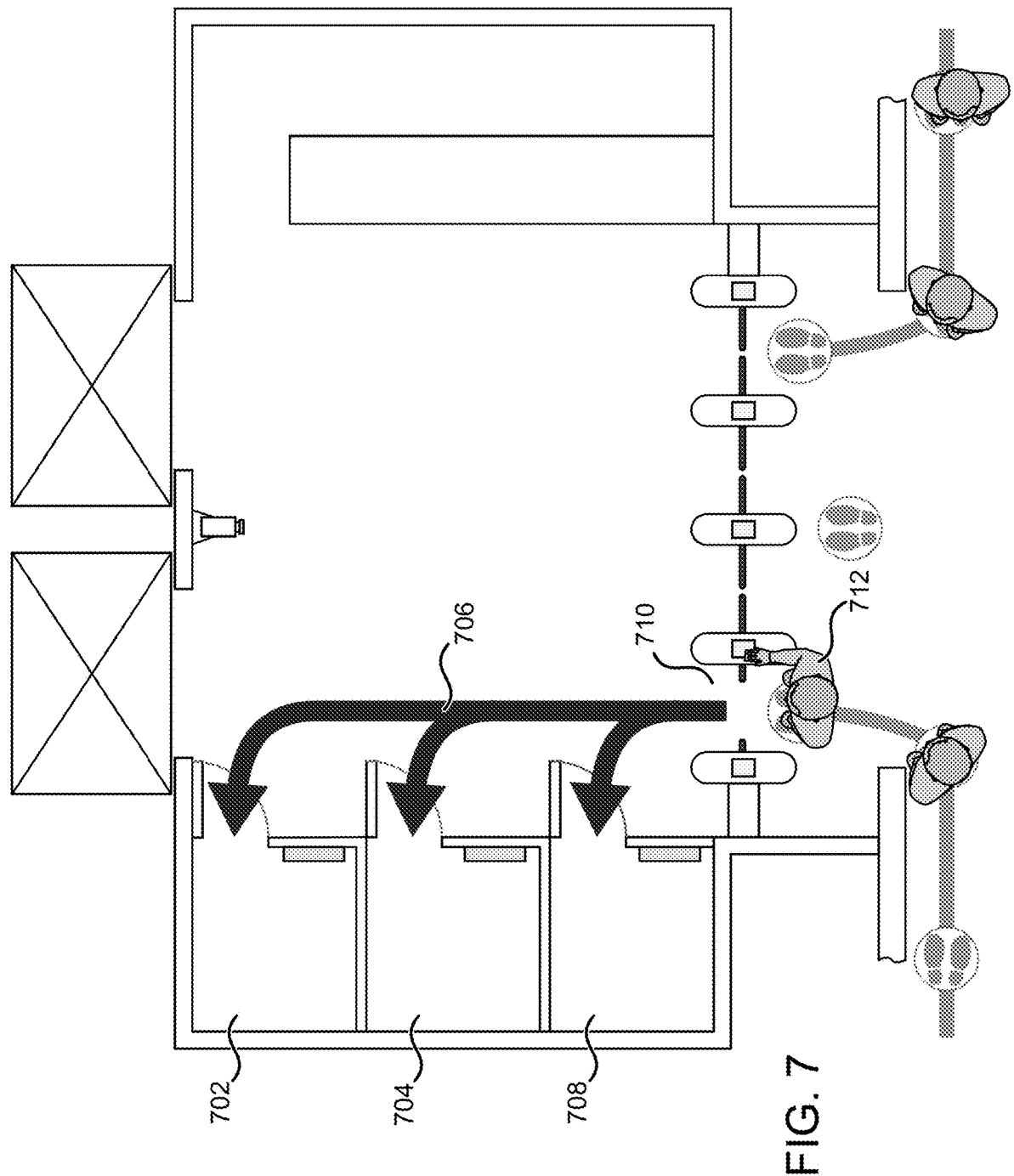
FIG. 7 is a diagram of a security system using contactless routing, which can be implemented in the system of FIG. 2, according to some embodiments.

Referring now to FIG. 7, operation of controller when a person is directed for testing is shown, according to some embodiments. Person 406 may present their ID card to turnstile 710. ACS 200 may then access their individual risks and determines that a test is required. Person 406 may then be directed to one of waiting rooms 702, 704, or 708, depending on which is currently available. Person 405 may then be presumed to take direct route 706. Finally, person 712 may self-administer a test or wait for a suitably qualified person to arrive to administer the test.

Figure 8:
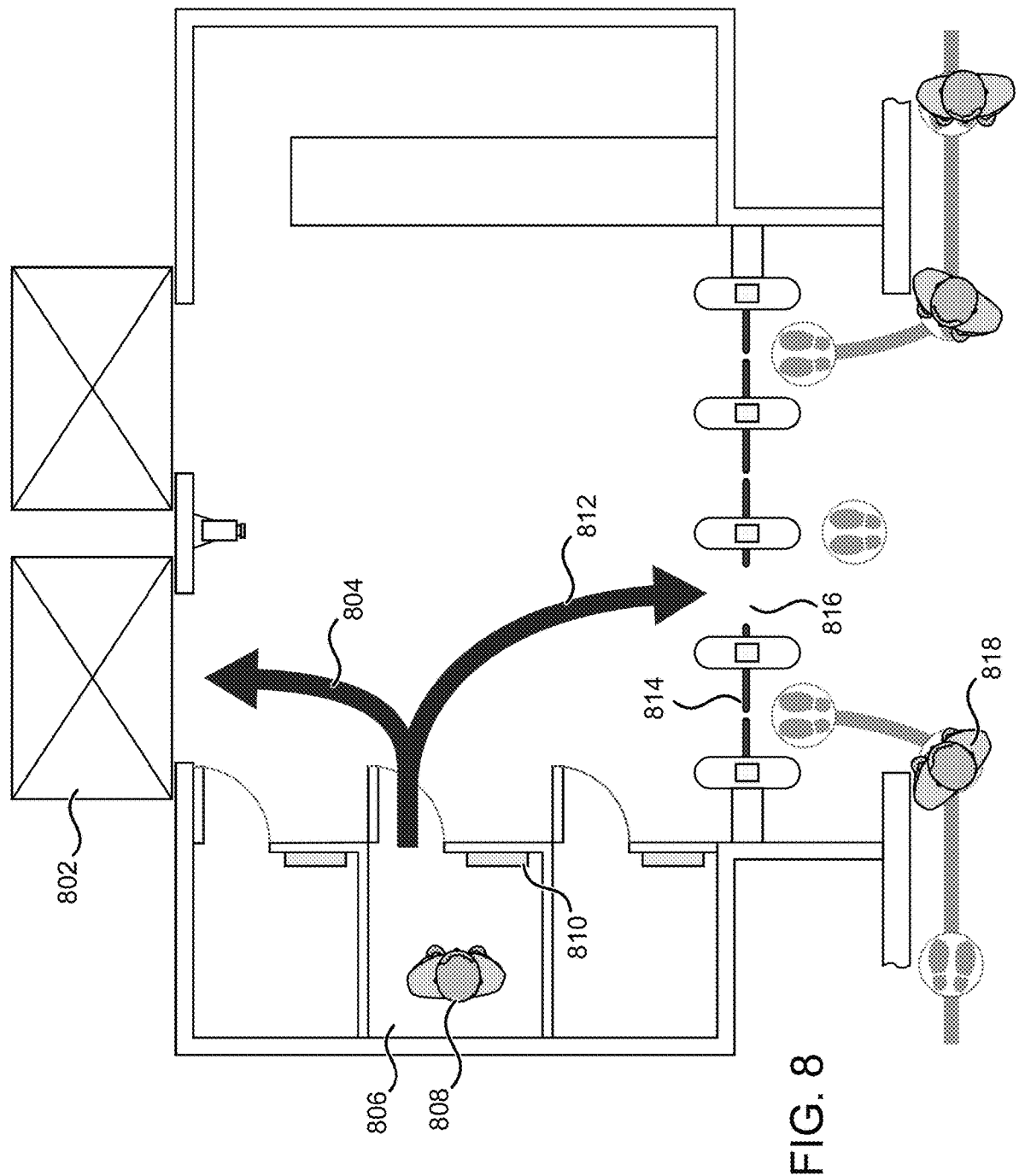
FIG. 8 is a diagram of a security system using contactless routing, which can be implemented in the system of FIG. 2, according to some embodiments.

Referring now to FIG. 8, an example of returning a test result is shown, according to some embodiments. Person 808 may remain in waiting room 806. After the test results are available, the results and further instructions are presented to person 808 on digital display 810, according to some embodiments. In the case of a negative result, person 808 may be directed to elevator 802 along route 804. In the case of a positive result, person 808 may be directed to exit the building through turnstile 816. A digital display on turnstile 814 may direct person 818 to move backwards to maintain required social distancing. Both the doors on elevator 802 and turnstile 816 may open automatically when required so that person 808 can exit without touching any of the surfaces.

Figure 9:
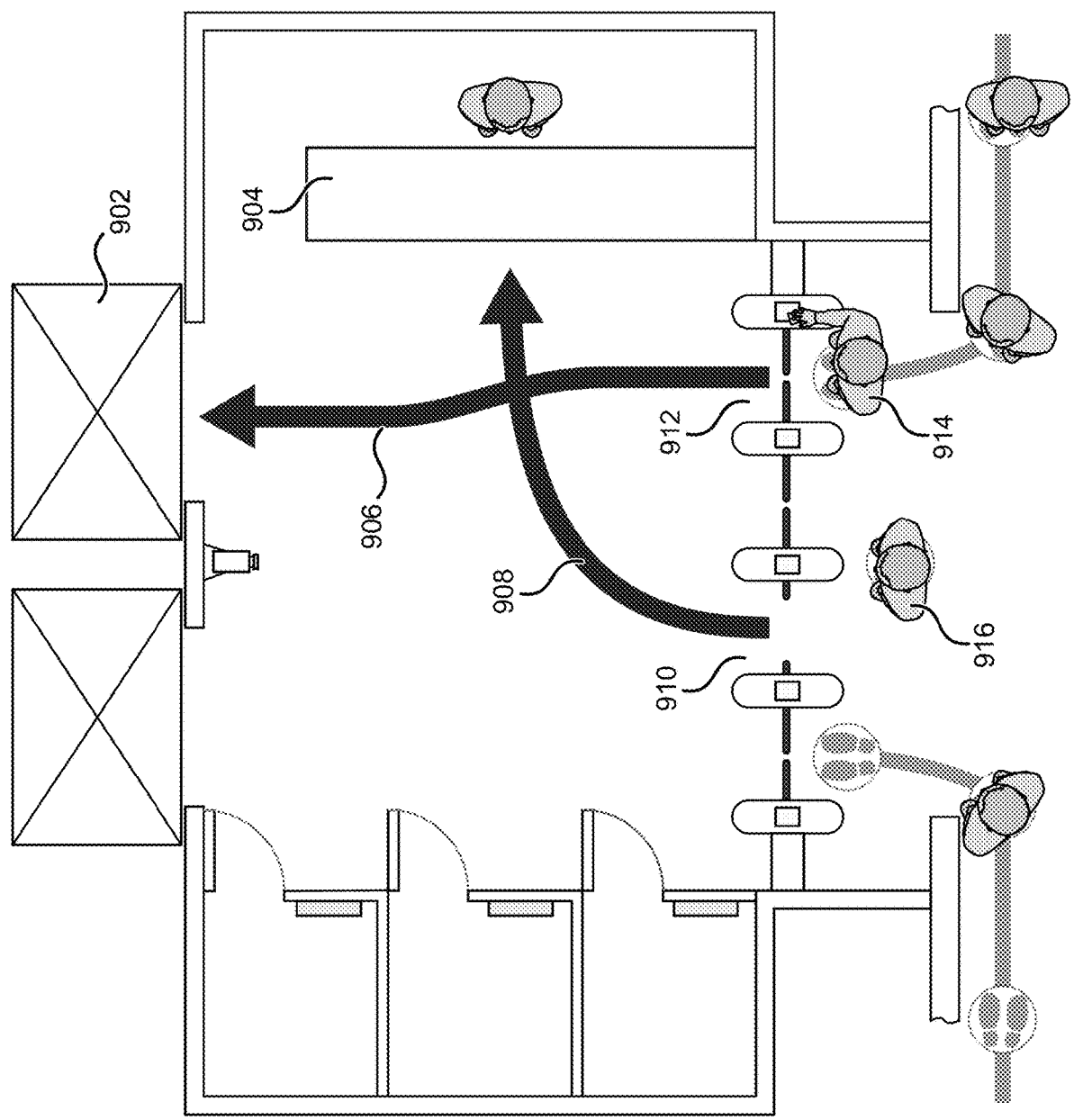
FIG. 9 is a diagram of a security system using contactless routing, which can be implemented in the system of FIG. 2, according to some embodiments.

Referring now to FIG. 9, an example of how controller 212 manages overlapping routes when directing people is shown, according to some embodiments. Person 916 may need to make a delivery to reception desk 904. Route 908 for person 908 may overlap with route 906 that person 914 would take to reach elevator 902. ACS 200 may open turnstile 910 but keep turnstile 912 closed to prevent a potential infringement of social distancing rules. Depending on the physical arrangement of the space, turnstile 912 may remain closed until person 916 completes their delivery and leaves through turnstile 910.

Configuration of Exemplary Embodiments

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device) may include one or more devices (e.g., RAM, ROM, Flash memory, hard disk storage) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions. "Non-transitory" excludes only mere signals in space, and includes all other forms of computer-readable storage media.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of various systems (e.g., system 100, system 200, etc.) and methods as shown in the various exemplary embodiments is illustrative only. Additionally, any element disclosed in one embodiment may be incorporated or utilized with any other embodiment disclosed herein. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. A method for providing access into a building, the method comprising:
   receiving an indication that a potential building occupant is requesting access into the building;
   providing input data into a probabilistic model, the input data comprising current health data of the potential building occupant obtained in response to receiving the indication;
   analyzing, via the probabilistic model, relationships between a plurality of variables within the probabilistic model to determine an entry decision for the potential building occupant, wherein each of the plurality of variables are representative of subsets of the input data;
   in response to the entry decision permitting the potential building occupant to enter the building, determining a testing center within the building to send the potential building occupant;
   providing audible or visual signals within the building to guide the potential building occupant to the testing center; and
   in response to determining that the potential building occupant has tested negative for a contagious disease, providing a control signal to a security system to permit access to the building for the potential building occupant.

2. The method of claim 1, wherein analyzing the relationships between the plurality of variables within the probabilistic model comprises:
   determining the subsets of the input data and dependencies between the subsets of the input data, wherein the plurality of variables represent the subsets of the input data and the relationships between the plurality of variables represent the dependencies between the subsets of the input data;
   determining a joint probability distribution between two or more of the plurality of variables;
   using the joint probability distribution to determine a probability of the potential building occupant having an infectious disease; and
   determining the entry decision for the potential building occupant.

3. The method of claim 1, wherein:
   the input data further comprises infectious risk data and profile data from a profile associated with the potential building occupant; and
   the subsets of the input data include at least one of local infection rate, contact tracing status, vaccination status, or temperature.

4. The method of claim 1, wherein:
   the probabilistic model is a Bayesian network model; and
   the plurality of variables are each weighted based on a likelihood that each of the plurality of variables would affect a probability of the potential building occupant having an infectious disease.

5. The method of claim 1, wherein the method further comprises:
   in response to the entry decision permitting the potential building occupant to enter the building, determining a location within the building to send the potential building occupant; and
   providing audible or visual signals within the building to guide the potential building occupant to the location; or
   providing instructions to a mobile device of the potential building occupant via a mobile application to guide the potential building occupant to the location.

6. The method of claim 1, wherein receiving the indication that the potential building occupant is requesting access into the building comprises receiving a request from the potential building occupant via a mobile application to enter the building.

7. A controller for providing access into a building, the controller comprising a processing circuit comprising one or more processors and memory, the memory storing instructions that, when executed by the one or more processors, cause the one or more processors to perform operations comprising:
   receiving an indication that a potential building occupant is requesting access into the building;
   providing input data into a probabilistic model, the input data comprising current health data of the potential building occupant obtained in response to receiving the indication;
   analyzing, via the probabilistic model, relationships between a plurality of variables within the probabilistic model to determine an entry decision for the potential building occupant, wherein each of the plurality of variables are representative of subsets of the input data, wherein analyzing the relationships between the plurality of variables within the probabilistic model comprises:
      determining the subsets of the input data and dependencies between the subsets of the input data, wherein the plurality of variables represent the subsets of the input data and the relationships between the plurality of variables represent the dependencies between the subsets of the input data;
      determining a joint probability distribution between two or more of the plurality of variables;
      using the joint probability distribution to determine a probability of the potential building occupant having an infectious disease;
      determining the entry decision for the potential building occupant; and
   in response to the entry decision permitting the potential building occupant to enter the building, providing a control signal to a security system to permit access to the building for the potential building occupant.

8. The controller of claim 7, wherein:
   the input data further comprises infectious risk data and profile data from a profile associated with the potential building occupant; and
   the subsets of the input data include at least one of local infection rate, contact tracing status, vaccination status, or temperature.

9. The controller of claim 7, wherein:
   the probabilistic model is a Bayesian network model; and
   the plurality of variables are each weighted based on a likelihood that each of the of plurality of variables would affect a probability of the potential building occupant having an infectious disease.

10. The controller of claim 7, the processing circuit is further configured to:
    in response to the entry decision permitting the potential building occupant to enter the building, determining a location within the building to send the potential building occupant; and
    providing audible or visual signals within the building to guide the potential building occupant to the location; or providing instructions to a mobile device of the potential building occupant via a mobile application to guide the potential building occupant to the location.

11. The controller of claim 7, wherein the processing circuit is further configured to:
in response to the entry decision permitting the potential building occupant to enter the building, determining a testing center within the building to send the potential building occupant;
providing audible or visual signals within the building to guide the potential building occupant to the testing center; and
in response to determining that the potential building occupant has tested negative for a contagious disease, providing access to the building for the potential building occupant.

12. The controller of claim 7, wherein receiving the indication that the potential building occupant is requesting access into the building comprises receiving a request from the potential building occupant via a mobile application to enter the building.

13. One or more non-transitory computer readable media having instructions stored thereon that, when executed by one or more processors, cause the one or more processors to implement operations comprising
receiving an indication that a potential building occupant is requesting access into a building;
providing input data into a probabilistic model, the input data comprising current health data of the potential building occupant obtained in response to receiving the indication;
analyzing, via the probabilistic model, relationships between a plurality of variables within the probabilistic model to determine an entry decision for the potential building occupant, wherein each of the plurality of variables are representative of subsets of the input data; and
in response to the entry decision permitting the potential building occupant to enter the building:
providing a control signal to a security system to permit access to the building for the potential building occupant;
determining a testing center within the building to send the potential building occupant;
providing audible or visual signals within the building to guide the potential building occupant to the testing center; and
in response to determining that the potential building occupant has tested negative for a contagious disease, providing a control signal to a security system to permit access to the building for the potential occupant.

14. The media of claim 13, wherein analyzing the relationships between the plurality of variables within the probabilistic model comprises:
determining the subsets of the input data and dependencies between the subsets of the input data, wherein the plurality of variables represent the subsets of the input data and the relationships between the plurality of variables represent the dependencies between the subsets of the input data;
determining a joint probability distribution between two or more of the plurality of variables;
using the joint probability distribution to determine a probability of the potential building occupant having an infectious disease; and
determining the entry decision for the potential building occupant.

15. The media of claim 13, wherein:
the input data further comprises infectious risk data and profile data from a profile associated with the potential building occupant; and
the subsets of the input data include at least one of local infection rate, contact tracing status, vaccination status, or temperature.

16. The media of claim 13, wherein:
the probabilistic model is a Bayesian network model; and
the plurality of variables are each weighted based on a likelihood that each of the plurality of variables would affect a probability of the potential building occupant having an infectious disease.

17. The media of claim 13, wherein the one or more processors are further configured to,
in response to determining that the potential building occupant has tested negative for a contagious disease, providing access to the building for the potential building occupant.

18. The media of claim 13, wherein receiving the indication that the potential building occupant is requesting access into the building comprises receiving a request from the potential building occupant via a mobile application to enter the building.

* * * * *